(12) United States Patent
Edwards, II et al.

(10) Patent No.: US 10,036,731 B2
(45) Date of Patent: Jul. 31, 2018

(54) WELD TESTING SYSTEM AND METHOD FOR A WELDING ASSEMBLY

(71) Applicants: Paul C. Edwards, II, Marysville, OH (US); Makoto Furukawa, Dublin, OH (US)

(72) Inventors: Paul C. Edwards, II, Marysville, OH (US); Makoto Furukawa, Dublin, OH (US)

(73) Assignee: Honda Motor Co., Ltd., Tokyo (JP)

( * ) Notice: Subject to any disclaimer, the term of this patent is extended or adjusted under 35 U.S.C. 154(b) by 141 days.

(21) Appl. No.: 15/087,461

(22) Filed: Mar. 31, 2016

(65) Prior Publication Data

US 2017/0284970 A1 Oct. 5, 2017

(51) Int. Cl.
*B23K 11/11* (2006.01)
*B23K 11/25* (2006.01)
*G01N 29/04* (2006.01)

(52) U.S. Cl.
CPC ..... *G01N 29/04* (2013.01); *G01N 2291/0234* (2013.01); *G01N 2291/0289* (2013.01)

(58) Field of Classification Search
CPC ....... B23K 11/11; B23K 11/25; B23K 11/251; B23K 11/252; B23K 11/255; B23K 11/256; B23K 11/257; B23K 11/258
USPC .................... 219/91.2, 108, 109, 110, 117.1; 73/587–588
See application file for complete search history.

(56) References Cited

U.S. PATENT DOCUMENTS

| | | | |
|---|---|---|---|
| 3,582,967 A * | 6/1971 | Beckman | B23K 11/25 219/109 |
| 4,019,364 A | 4/1977 | Maddox | |
| 5,575,934 A | 11/1996 | Takakuwa et al. | |
| 5,721,415 A | 2/1998 | Fortmann et al. | |
| 6,043,449 A | 3/2000 | Kanjo | |
| 6,583,386 B1 | 6/2003 | Ivkovich | |
| 7,304,268 B2 | 12/2007 | Burt et al. | |
| 8,552,337 B2 | 10/2013 | Albrecht | |
| 2004/0129081 A1* | 7/2004 | Stauffer | G01L 3/24 73/588 |
| 2005/0126293 A1* | 6/2005 | Dasch | G01N 29/225 73/618 |
| 2011/0278786 A1* | 11/2011 | Yamagishi | B65H 7/125 271/18 |
| 2013/0075371 A1 | 3/2013 | De Souza et al. | |

(Continued)

*Primary Examiner* — Peter Macchiarolo
*Assistant Examiner* — Anthony W Megna Fuentes
(74) *Attorney, Agent, or Firm* — Armstrong Teasdale LLP

(57) ABSTRACT

A non-destructive weld testing system for testing spot welds includes a weld monitoring tool monitoring at least one weld characteristic of the spot welds and generating weld data based on the at least one weld characteristic; a weld analysis tool analyzing the weld data to determine a weld quality of each spot weld based on analysis criteria; and a non-destructive weld testing tool configured to test spot welds. The weld testing system causes the weld testing tool to target testing of spot welds determined by the weld analysis tool to have a weld quality beyond a threshold weld quality. The weld testing tool may be a robot-mounted phased array transducer generating weld test data based on testing results and provides feedback to the weld analysis tool correlating to the weld test data. The weld analysis tool updates the analysis criteria based on the weld test data.

20 Claims, 3 Drawing Sheets

(56) References Cited

U.S. PATENT DOCUMENTS

2013/0112678 A1    5/2013  Park et al.
2015/0108100 A1\*  4/2015  Haeufgloeckner .. B23K 31/125
                                                  219/109

\* cited by examiner

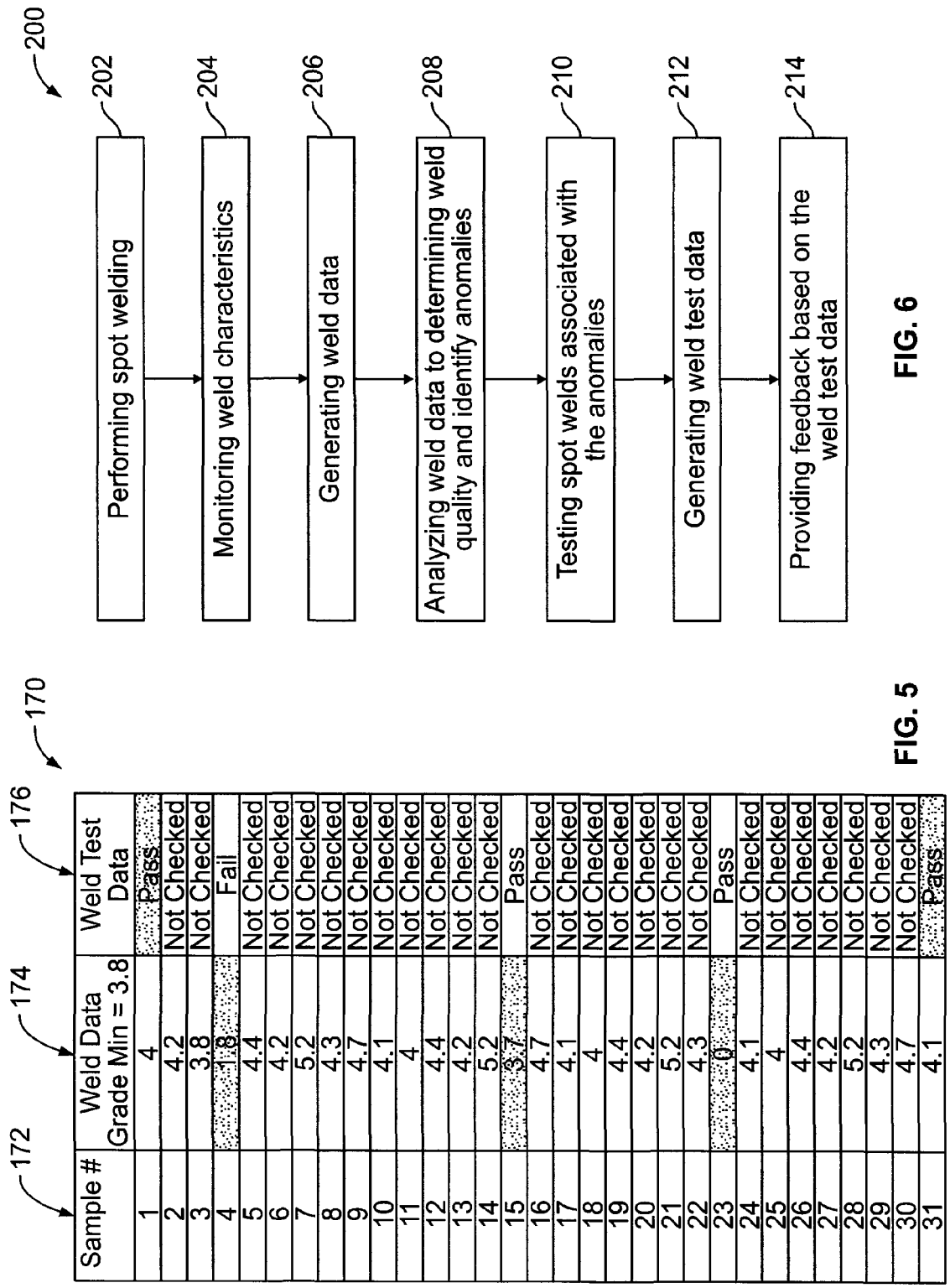

FIG. 5

| Sample # | Weld Data Grade Min = 3.8 | Weld Test Data |
|---|---|---|
| 1 | 4 | Pass |
| 2 | 4.2 | Not Checked |
| 3 | 3.8 | Not Checked |
| 4 | 1.8 | Fail |
| 5 | 4.4 | Not Checked |
| 6 | 4.2 | Not Checked |
| 7 | 5.2 | Not Checked |
| 8 | 4.3 | Not Checked |
| 9 | 4.7 | Not Checked |
| 10 | 4.1 | Not Checked |
| 11 | 4 | Not Checked |
| 12 | 4.4 | Not Checked |
| 13 | 4.2 | Not Checked |
| 14 | 5.2 | Not Checked |
| 15 | 3.7 | Pass |
| 16 | 4.7 | Not Checked |
| 17 | 4.1 | Not Checked |
| 18 | 4 | Not Checked |
| 19 | 4.4 | Not Checked |
| 20 | 4.2 | Not Checked |
| 21 | 5.2 | Not Checked |
| 22 | 4.3 | Not Checked |
| 23 | 0 | Pass |
| 24 | 4.1 | Not Checked |
| 25 | 4 | Not Checked |
| 26 | 4.4 | Not Checked |
| 27 | 4.2 | Not Checked |
| 28 | 5.2 | Not Checked |
| 29 | 4.3 | Not Checked |
| 30 | 4.7 | Not Checked |
| 31 | 4.1 | Pass |

FIG. 6

200 → 202 Performing spot welding → 204 Monitoring weld characteristics → 206 Generating weld data → 208 Analyzing weld data to determining weld quality and identify anomalies → 210 Testing spot welds associated with the anomalies → 212 Generating weld test data → 214 Providing feedback based on the weld test data

WELD TESTING SYSTEM AND METHOD FOR A WELDING ASSEMBLY

BACKGROUND

The present disclosure relates generally to a weld testing system and method of welding assemblies for testing spot welds.

On automotive assembly lines, much of the assembly process involves welding operations by welding assemblies using robotic welders. The welding assemblies used for resistance welding have electrode tips that are used for spot welding metal pieces together. Welding is a critical process that impacts many parts of the automobile, including the performance of the parts in the completed vehicle. The quality of each weld not only has an impact on consumer concerns such as alignment of the body parts, ride and noise, and longevity of the vehicle, but also has a direct impact on manufacturing cycle time, scrap, downtime, and overall costs.

The welding assemblies are subject to various problems that impact the quality of the weld. System parts wear out over time and in other cases, may be damaged or simply fail for a variety of reasons. As welding tips and other parts of the welding assembly wear or fail, the integrity of the weld begins to diminish. Weld inspection is performed to check the quality of the welding process for prevention and detection of weld failures prior to the vehicles leaving the assembly plant. Conventional weld inspection systems periodically check random spot welds, such as every $30^{th}$ spot weld, to determine if the weld quality is maintained. However, such systems suffer from the problem that some bad welds will be missed prior to the random checking process identifying that the welding assembly is improperly working. It is impractical to check every spot weld as the testing process would slow the overall vehicle assembly time.

A need remains for a weld testing system capable of inspecting spot welds in a cost effective and reliable manner.

BRIEF DESCRIPTION

In one embodiment, a welding assembly is provided for in-line spot welding using welding electrodes of a welding machine. The welding assembly includes a non-destructive weld testing system configured to monitor the welding electrodes during spot welding of the spot welds and analyze weld data generated during the spot welding. The weld testing system has a non-destructive weld testing tool mounted on a robot and being robotically controlled. The weld testing tool has a phased-array ultrasonic transducer configured to test spot welds in-line that are determined by the weld testing system to be anomalies.

In another embodiment, a non-destructive weld testing system for testing spot welds performed by welding electrodes of a welding machine is provided that includes a weld monitoring tool monitoring at least one weld characteristic of the spot welds and generating weld data based on the at least one weld characteristic. The weld testing system includes a weld analysis tool analyzing the weld data to determine a weld quality of each spot weld based on analysis criteria. The weld testing system includes a non-destructive weld testing tool configured to test spot welds. The weld testing system causes the weld testing tool to target testing of spot welds determined by the weld analysis tool to have a weld quality beyond a threshold weld quality. The weld testing tool generates weld test data based on testing results and provides feedback to the weld analysis tool correlating to the weld test data. The weld analysis tool updates the analysis criteria based on the weld test data.

In a further embodiment, a method of non-destructive weld testing spot welds performed by welding electrodes of a welding machine is provided that includes monitoring at least one weld characteristic of the spot welds, generating weld data based on the at least one weld characteristic, analyzing the weld data to determine a weld quality of each spot weld based on analysis criteria to determine spot welds that are anomalies, testing spot welds determined to be anomalies, generating weld test data based on testing results of the tested spot welds, and providing feedback correlating to the weld test data to update the analysis criteria based on the weld test data.

BRIEF DESCRIPTION OF THE DRAWINGS

FIG. 5 is a weld analysis database showing weld samples, weld data and weld test data.

FIG. 6 illustrates a non-destructive weld testing method in accordance with an exemplary embodiment.

DETAILED DESCRIPTION

Various embodiments of methods and systems for non-destructive weld testing of spot welds are provided. It should be noted that although the various embodiments are described in connection with the automotive industry, such as for an automobile assembly process, one or more embodiments may be implemented in different industries and for different applications.

One or more embodiments include a weld testing system used to identify anomalies in spot welds and target testing of such identified spot welds. The weld testing system analyzes weld data in real time to quickly identify suspect or bad spot welds so that such spot welds can be tested quickly before additional problem or bad welds are made by the welding assembly. The weld testing system generates test weld data from the testing results and provides feedback, such as to update the analysis criteria for analyzing the weld data. A dynamic weld testing system is provided that may be used in-line during the automobile assembly process to detect and prevent weld failures in mass production.

Figure 1:
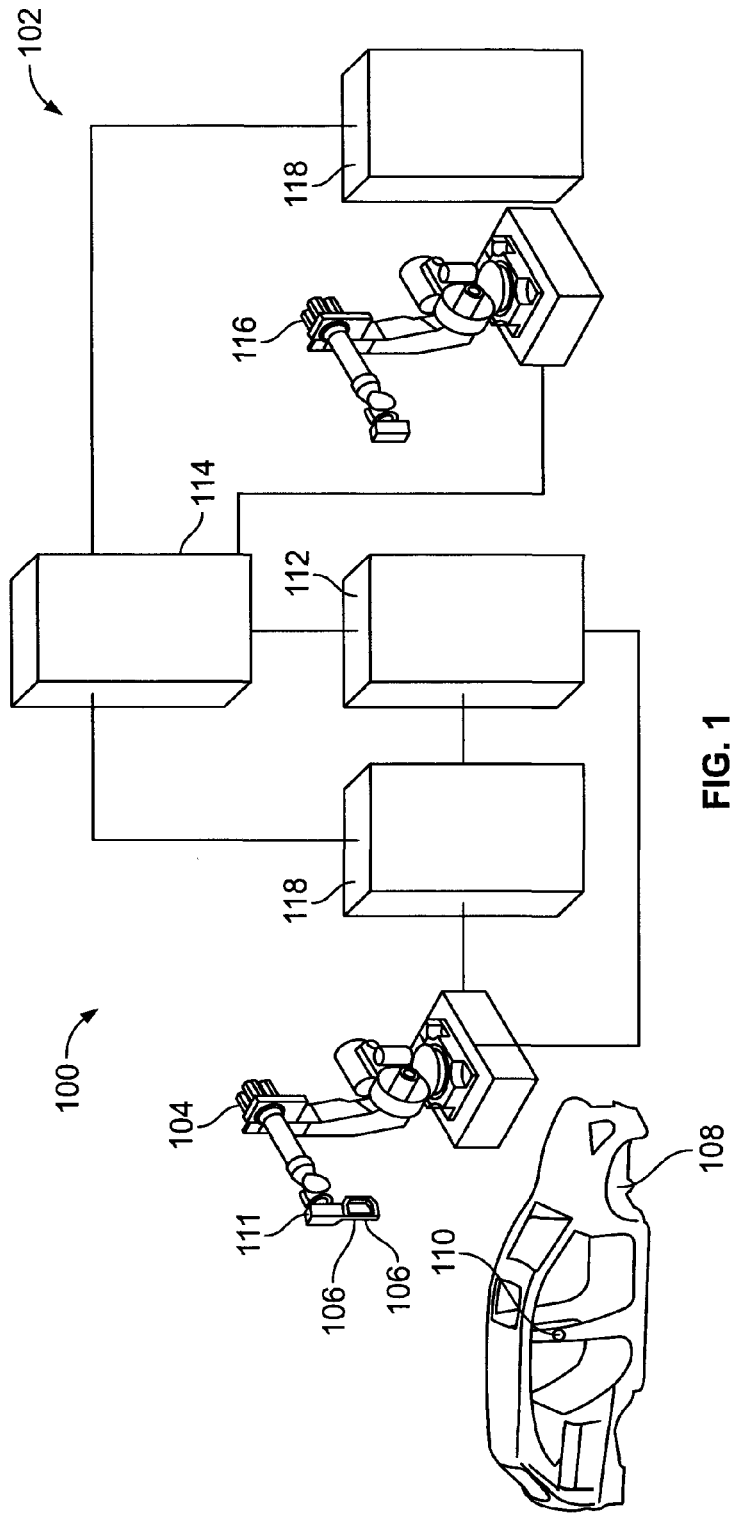
FIG. 1 is a block diagram of a welding assembly that uses a weld testing system in accordance with one embodiment.

FIG. 1 is a block diagram of a welding assembly 100 that uses a weld testing system 102 in accordance with one embodiment. The welding assembly 100 is used for in-line spot welding, such as in mass production of an automobile assembly process. The welding assembly 100 includes a welding robot 104 having one or more arms configured to move in three dimensional space (e.g., movable in X, Y and Z directions). The welding robot 104 has electrode tips 106 at an end of the arm. The electrode tips 106 are configured for use in resistance welding, such as for spot welding a component 108 (the spot weld is identified at 110). The welding process may be controlled to control the amount of heat or energy delivered to the spot. For example, weld characteristics such as, but not limited to, the current, voltage, resistance, heat input rate, total energy input, weld time or duration, and the like may be controlled, and may be different for different spot welds 110.

The weld testing system 102 monitors the welding process at each spot weld 110, such as by monitoring one or more weld characteristics of the welding process to identify anomalies. The weld testing system 102 may include one or more sensors 111 monitoring or measuring one or more elements of the welding operation, such as operation of the electrode tips 106 of the welding robot 104 and/or the circuit powering the electrode tips 106 during the welding process. The weld testing system 102 tests the spot welds 110, such as the spot welds 110 that have identified anomalies. It is noted that typical automobiles have many spot welds 110 each being monitored and capable of being tested, such as if the weld testing system 102 determines that a particular spot weld 110 has an anomaly.

In various embodiments, it may be desirable to use many welding robots 104 and many weld testing systems 102 in one or more stations along the assembly line. The weld testing system 102 is operated in real-time during the welding process of the automobile and is operated in-line with the welding robot 104. Other stations may be added as desired in-line in the vehicle assembly line process.

In an exemplary embodiment, the weld testing system 102 includes a weld monitoring tool 112 monitoring at least one weld characteristic of the spot welds 110 and generating weld data based on the at least one weld characteristic. The weld data may be stored in a database. The weld testing system 102 includes a weld analysis tool 114 analyzing the weld data to determine a weld quality of each spot weld 110 based on analysis criteria. The weld testing system 102 includes a non-destructive weld testing tool 116 configured to test spot welds 110. In an exemplary embodiment, the weld testing tool 116 may be an ultrasonic transducer. Optionally, the weld testing tool 116 may be a phased array ultrasonic transducer. In other various embodiments, the weld testing tool 116 may be another type of non-destructive weld testing tool, such as a thermographic camera, an infra-red testing system, and the like.

In operation, the weld testing system 102 causes the weld testing tool 116 to target testing of spot welds 110 determined by the weld analysis tool 114 to have anomalies, such as those spot welds 110 having a weld quality beyond a threshold weld quality. The weld testing tool 116 generates weld test data based on testing results and provides feedback to the weld analysis tool 114 corresponding to the weld test data. For example, the weld test data may relate to a quality of the weld nugget formed, such as a diameter or shape of the weld nugget. The weld analysis tool 114 updates the analysis criteria based on the weld test data. For example, if the weld testing tool 116 determines that the flagged spot weld 110, which was identified as being an anomaly, is actually a good spot weld, then the thresholds or other analysis criteria used to flag suspect spot welds may be updated so that future spot welds 110 having the same weld data are not flagged as being anomalies. Such feedback allows the weld testing system 102 to update the weld quality analysis based on actual measured results and such updates may be performed in real-time as the assembly process continues.

A control module 118 is operably coupled to the welding robot 104 and the weld testing tool 116. Optionally, the welding robot 104 and the weld testing tool 116 may be coupled to separate control modules 118 rather than the same control module 118. The control module 118 controls movement of the welding robot 104, such as to control the position of the electrode tips 106 during the welding process. The control module 118 may be operably coupled to the electrode tips 106, such as to control an ON/OFF state or other weld characteristics of the electrode tips 106 during welding. The control module 118 controls movement of the weld testing tool 116, such as to move the weld testing tool 116 into position to test a particular spot weld. The control module 118 may be operably coupled to the weld testing tool 116, such as to control an ON/OFF state of the weld testing tool 116 during testing.

The control module 118 may form part of or be embodied as one or more computing systems, such as one or more PLCs. It should be noted that while a particular computing or operating environment may be described herein, the computing or operating environment is intended to illustrate operations or processes that may be, implemented, performed, and/or applied to a variety of different computing or operating environments. Thus, FIG. 1 illustrates a non-limiting example of a controller that may perform one or more methods or processes as described in more detail herein.

The control module 118 may be provided, for example, as any type of computing device, including, but not limited to PLCs or personal computing systems, among others. The control module 118 may optionally include components not shown in FIG. 1, and/or some components shown in FIG. 1 may be peripheral components that do not form part of or are not integrated into the computing system. The control module 118 may include one or more physical devices configured to execute one or more instructions. For example, the control module 118 may be configured to execute one or more instructions that are part of one or more programs, routines, objects, components, data structures, or other logical constructs. Such instructions may be implemented to perform a task, implement a data type, transform the state of one or more devices, or otherwise arrive at a desired result.

The control module 118 may include one or more processors and/or computing devices that are configured to execute software instructions, such as programmed using application software. In some embodiments, one or more algorithms as described herein are embedded into the PLC. Additionally or alternatively, the control module 118 may include one or more hardware or firmware logic machines configured to execute hardware or firmware instructions. The control module 118 may optionally include individual components that are distributed throughout two or more devices, which may be remotely located in some embodiments.

Thus, the various components, subsystems, or modules of the control module 118 may be implemented in hardware, software, or a combination thereof, as described in more detail herein. Additionally, the processes, methods, and/or algorithms described herein may be performed using one or more processors, processing machines or processing circuitry to implement one or more methods described herein. Optionally, the various components may be integrated into common module(s). For example, the control module 118, weld monitoring tool 112, weld analysis tool and/or the weld testing tool may be integrated into a common control module or computing device.

Figure 2:
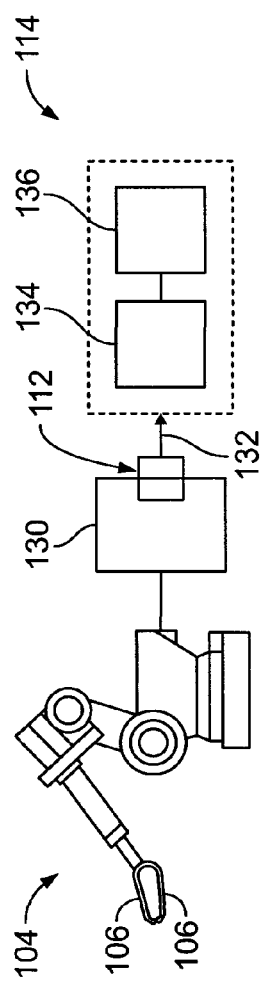
FIG. 2 is a schematic diagram of a weld monitoring tool of the weld testing system in accordance with an exemplary embodiment.

FIG. 2 is a schematic diagram of the weld monitoring tool 112 in accordance with an exemplary embodiment. The weld monitoring tool 112 is coupled to a welding circuit 130 of the welding robot 104. The welding circuit 130 provides power to the electrode tips 106. The weld monitoring tool 112 monitors the welding circuit 130. The weld monitoring tool 112 may be a sensor monitoring the welding circuit 130 or another portion of the welding robot 104 or electrode tips 106. For example, the weld monitoring tool 112 may measure the current, the voltage, the resistance or other weld characteristics of the welding circuit 130. The weld monitoring tool 112 may monitor the welding circuit 130 along any point thereof and at any time. The weld monitoring tool 112 may calculate other weld characteristics of the welding circuit 130 based on the measured characteristics. In various embodiments, the calculated characteristics include the heat input rate, total energy input, the weld time or weld duration, and the like, which may be calculated based on formulas or algorithms using measured characteristics, coefficients or other variables as inputs.

The weld monitoring tool 112 generates weld data 132 based on the measured and/or calculated weld characteristics. The weld data 132 is used by the weld analysis tool 114. For example, the weld data 132 may be transmitted to a database 134 of the weld analysis tool 114. An analysis module 136 of the weld analysis tool 114 may execute a software application that calculates a quality of the spot weld based on the weld data 132. The database 134 and/or the analysis module 136 may be accessible through multiple networked computers and the weld analysis tool 114 may be implemented in a variety of ways so that it is accessible to numerous computer users.

The weld data 132 may include data for more than one weld characteristic. For example, weld data 132 relating to any or all of the current, voltage, resistance, heat input rate, total energy input, weld time or duration, or other characteristics may be used by the weld analysis tool 114 to analysis the weld quality. The weld monitoring tool 112 performs the data gathering during the welding process based on the operation of the welding robot 104, and such data is then used by the weld analysis tool 114 to determine weld quality of each of the spot welds. The weld data 132 may be time stamped to correlate the weld data 132 with a particular spot weld 110.

The weld analysis tool 114 may form part of or be embodied as one or more computing systems, such as one or more PLCs. It should be noted that while a particular computing or operating environment may be described herein, the computing or operating environment is intended to illustrate operations or processes that may be, implemented, performed, and/or applied to a variety of different computing or operating environments. Thus, FIG. 2 illustrates a non-limiting example of a module that may perform one or more methods or processes as described in more detail herein.

The weld analysis tool 114 may be provided, for example, as any type of computing device, including, but not limited to PLCs or personal computing systems, among others. The weld analysis tool 114 may optionally include components not shown in FIG. 2, and/or some components shown in the Figures may be peripheral components that do not form part of or are not integrated into the computing system. The weld analysis tool 114 may include one or more physical devices configured to execute one or more instructions. For example, the weld analysis tool 114 may be configured to execute one or more instructions that are part of one or more programs, routines, objects, components, data structures, or other logical constructs. Such instructions may be implemented to perform a task, implement a data type, transform the state of one or more devices, or otherwise arrive at a desired result.

The weld analysis tool 114 may include one or more processors and/or computing devices that are configured to execute software instructions, such as programmed using application software. In some embodiments, one or more algorithms as described herein are embedded into the PLC. Additionally or alternatively, the weld analysis tool 114 may include one or more hardware or firmware logic machines configured to execute hardware or firmware instructions. The weld analysis tool 114 may optionally include individual components that are distributed throughout two or more devices, which may be remotely located in some embodiments.

Thus, the various components, subsystems, or modules of the weld analysis tool 114 may be implemented in hardware, software, or a combination thereof, as described in more detail herein. Additionally, the processes, methods, and/or algorithms described herein may be performed using one or more processors, processing machines or processing circuitry to implement one or more methods described herein.

Figure 3:
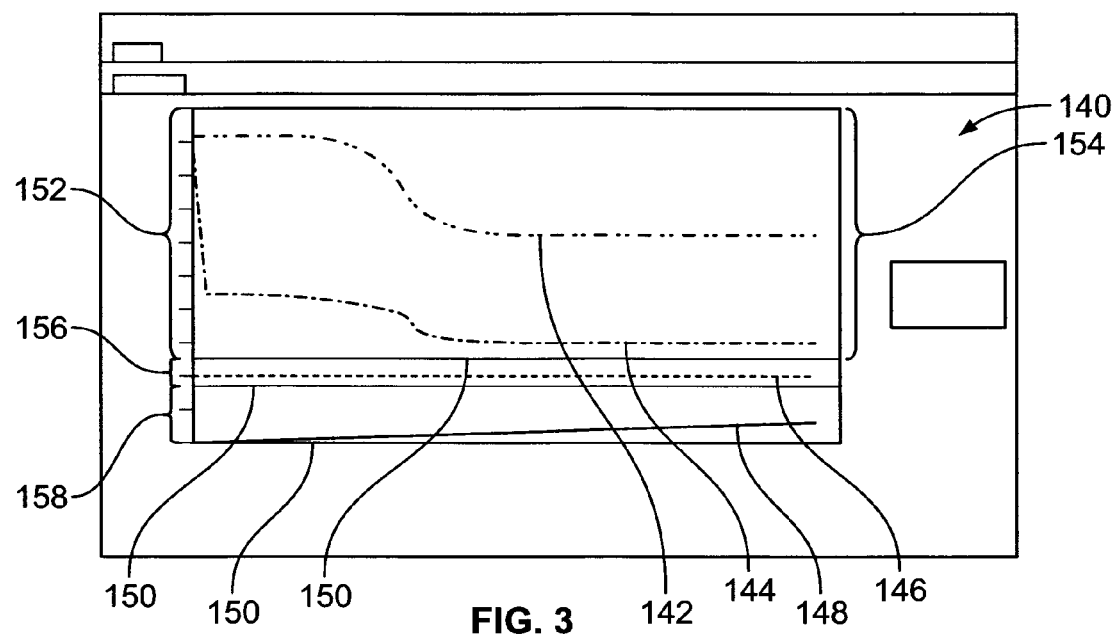
FIG. 3 is a weld data graph or plot showing weld data taken during a spot welding process in accordance with an exemplary embodiment.

FIG. 3 is a weld data graph or plot 140 showing weld data taken during a spot welding process in accordance with an exemplary embodiment. The plot 140 shows first weld data 142, second weld data 144, third weld data 146 and fourth weld data 148 plotted along a time axis 150. The weld data 142, 144, 146, 148 represents different types of weld data for the same spot weld 110. For example, the first weld data 142 may be resistance weld data plotted against a first axis 152, the second weld data 144 may be current weld data plotted against a second axis 154, the third weld data 146 may be heat input weld data plotted against a third axis, and the fourth weld data 148 may be total energy input data plotted against a fourth axis. Such plot 140 may be analyzed to identify trends, anomalies, and the like. For example, the weld analysis tool 114 may analyze the data in the plot 140 to identify trends, anomalies, and the like. The weld analysis tool 114 may analyze the weld data 142, 144, 146, 148 individually. Optionally, the weld analysis tool 114 may identify anomalies based on any of the weld data 142, 144, 146, 148, such as if any of the weld data 142, 144, 146, 148 is suspect. In other various embodiments, the weld analysis tool 114 may identify anomalies based on a combined analysis of more than one of the weld data 142, 144, 146, 148. For example, if one of the weld data 142, 144, 146, 148 is suspect, the weld analysis tool 114 may analyze the other weld data 142, 144, 146, 148 before determining that the spot weld is bad. The weld analysis tool 114 may look at other weld data other than the weld data 142, 144, 146, 148 shown in FIG. 3. The weld analysis tool 114 is computerized and may execute a software application that calculates a quality of the spot weld.

Figure 4:
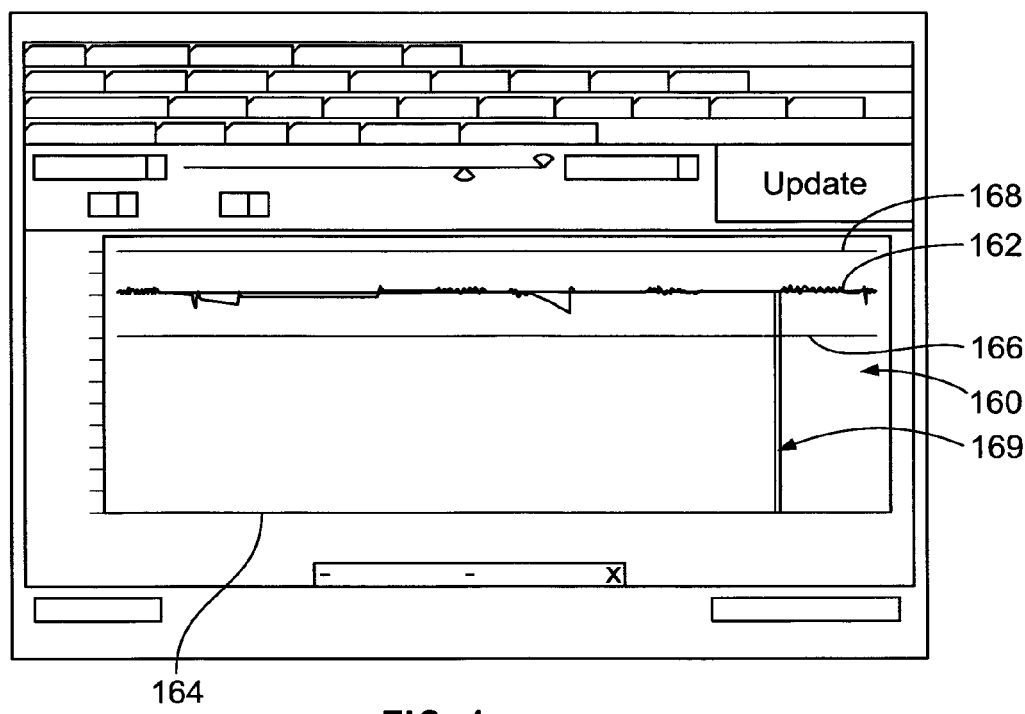
FIG. 4 is a weld data graph or plot showing weld data taken during a spot welding process in accordance with an exemplary embodiment.

FIG. 4 is a weld data graph or plot 160 showing weld data taken during a spot welding process in accordance with an exemplary embodiment. The plot 160 shows weld data 162 plotted along a time axis 164. The plot 160 shows a minimum threshold 166 and a maximum threshold 168. The thresholds 166, 168 define analysis criteria for determining a quality of the spot weld 110. Other types of analysis criteria may be used in alternative embodiments, such as variance or deviation from a target, negative trends, rate of change in weld data, and the like.

A portion of the weld data 162 may exceed a tolerance, such as fall below the minimum threshold 166 or rise above the maximum threshold 168, corresponding to an anomaly 169 indicating a problem with the welding operation at the indicated time. The weld analysis tool 114 is able to identify such anomalies 169 to identify the corresponding spot weld as a suspect spot weld that should be checked or tested to verify whether or not the spot weld is a bad weld or a good weld.

In operation, the weld analysis is used to target testing of particular spot welds 110 that are suspected as being bad welds. The weld testing system 102 causes the weld testing tool 116 to test each suspect spot weld 110 having an anomaly. The weld analysis tool 114 triggers the weld testing system 102 to test the suspect spot welds 110. Optionally, the weld testing system 102 may sample spot welds 110 at predetermined intervals in addition to the triggered or suspected spot welds 110. For example, the weld testing system 102 may cause every Nth spot weld (e.g., every 30$^{th}$ spot weld) to be tested.

After the weld testing tool 116 tests the spot weld 110 to verify the quality of the spot weld 110, the analysis criteria may be updated. For example, if a particular spot weld was identified as being bad or suspect and verified by the weld testing tool 116 to be a bad weld, then feedback may be provided to the weld analysis tool 114 to enforce the analysis criteria. If a particular spot weld was identified as being bad or suspect, but the spot weld was verified by the weld testing tool 116 as being a good weld, then such feedback is provided to the weld analysis tool 114, such as to change the analysis criteria. For example, the minimum threshold 166 may be lowered or the maximum threshold may be raised. If a spot weld was identified as being a good weld but the spot weld was randomly tested anyway, feedback about such spot weld may be provided to the weld analysis tool 114 to enforce the analysis criteria.

FIG. 5 is a weld analysis database 170 showing weld samples 172, weld data 174 and weld test data 176. The weld samples may be sample spot welds from the same welding robot 104 or from multiple robots. The weld samples may be arranged chronologically. Optionally, the weld testing system 102 may cause every Nth spot weld (e.g., every 30$^{th}$ spot weld) to be tested. For example, weld sample 1 and weld sample 31 (and weld sample 61, etc.) may be tested by the weld testing tool 116.

The weld data 174 may be any type of weld data. The weld data 174 may relate to any type of weld characteristic, such as total energy input. Weld data 174 is provided for each weld sample 172. Optionally, if no weld data is gathered for a weld sample 172, the weld testing system 102 may be triggered to flag the corresponding spot weld for testing. The weld analysis tool 114 analyzes the weld data to determine a weld quality of each sample based on certain analysis criteria specific to the type of weld data 174. The weld data 174 may have a threshold, such as a minimum threshold. In the illustrated embodiment, the minimum threshold is 3.8; however any threshold may be used in alternative embodiments and the threshold may depend on the analysis criteria and the type of weld data. Optionally, if the weld data 174 is determined to have a weld quality beyond a threshold weld quality, the weld testing system 102 may be triggered to flag the corresponding spot weld for testing. For example, if the weld data 174 is within the threshold of the analysis criteria, the sample may receive a pass grade, but if the weld data 174 is beyond the threshold of the analysis criteria, the sample may receive a fail grade. All samples that have a fail grade may be flagged for testing by the weld testing tool 116. In the illustrated embodiment, it is shown that weld samples 4 and 15 are beyond the threshold and are flagged for testing. Weld sample 23 shows no data and is also flagged for testing. Weld samples 1 and 31 are also flagged for testing; however in other embodiments the system may skip to the Nth spot weld after the previously tested sample. For example, in this case, instead of testing sample 31, the weld testing system 102 would have sample 53 tested, as sample 53 is 30 welds after sample 23, unless another bad weld is detected prior to sample 53.

The weld test data 176 shows results of the weld testing. In the illustrated embodiment, sample 1 was tested and passed as a good weld; sample 4 was tested and failed as confirming that the spot weld was a bad weld; sample 15 was tested and passed even though the weld data indicated such weld as being a bad weld; sample 23 was tested and passed; and sample 31 was tested and passed as a good weld. Testing samples 1 and 31 verify operation of the weld testing system 102 and occur even if the weld analysis tool 114 is not indicating that any welds are bad welds. Testing of sample 23 occurred because no data was gathered about the particular weld, which could occur when the welding robot 104 malfunctions, thus forming no weld, or when the weld monitoring tool 112 is not working or because of other factors. Testing of sample 4 verifies that the analysis criteria is actually identifying suspect or bad welds and may provide useful feedback to the weld analysis tool 114 that the analysis criteria is properly set, allowing the weld testing system 102 to identify the bad weld for repair or scrap as opposed to allowing the vehicle to continue assembly even though it is defective. Testing of sample 15 identifies a potential problem with the analysis criteria used by weld analysis tool 114 in that the weld analysis tool 114 identified the weld as being bad; however the testing determined that the weld was good. Feedback may be provided to the weld analysis tool 114 to update the analysis criteria. Optionally, the update criteria may not be updated based on a single event, but may require multiple negative feedback before the analysis criteria is updated.

FIG. 6 illustrates a non-destructive weld testing method 200 in accordance with an exemplary embodiment. The method 200, for example, may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 200 may be able to be used as one or more algorithms to direct hardware to perform operations described herein.

The method 200 includes performing 202 spot welding using welding electrodes of a welding machine. The spot welding is performed in accordance with certain welding characteristics. The welding characteristics may be different for different spot welds, such as at different locations of the vehicle. The welding characteristics may include current, voltage, resistance, heat input rate, total energy input, weld time or duration, and the like.

The method 200 includes monitoring 204 at least one weld characteristic of the spot welds. The weld characteristics may be monitored using a weld monitoring tool. The weld characteristics may be monitored using sensors, timers, hardware devices, or other devices, which may be coupled to the welding electrodes and/or the welding circuit of the welding machine.

The method 200 includes generating 206 weld data based on the at least one weld characteristic that is monitored. The weld data may be generated by the weld monitoring tool, a weld analysis tool, a control module or other device. The weld data may be generated by measuring physical or electrical properties of the welding electrodes or spot weld. The weld data may be generated by calculating weld characteristics based on other measured characteristics, such as using software or algorithms. The weld data may be stored in a database.

The method 200 includes analyzing 208 the weld data to determine a weld quality of each spot weld. The weld data may be analyzed by a weld analysis tool. The weld data may be analyzed based on analysis criteria to determine spot welds that are anomalies. For example, the weld analysis tool may have thresholds or other analysis criteria to compare the weld data to. The weld analysis tool may have different look-up tables for different weld characteristics used to determine a weld quality. The weld analysis tool may base the weld quality determination on multiple weld characteristics. The weld analysis tool may provide a grade, such as a pass grade or a fail grade, to each spot weld. The weld analysis tool identifies spot welds that are suspected of being bad welds.

The method 200 includes testing 210 spot welds determined to be anomalies. The spot welds may be tested by a weld testing tool. The spot welds may be tested using a non-destructive testing device or tool. The spot welds may be tested by an ultrasound device, such as a phased array ultrasound transducer, by a thermographic camera, such as an IR camera, and the like. The spot welds may be tested by measuring a weld nugget diameter or shape. The spot weld may be tested by passing ultrasound through the spot weld in more than one direction or angle. The weld testing tool may be robotically controlled, such as being mounted to an end of an arm of a robot. The weld testing tool may be operated without an operator holding or positioning the weld testing tool. Having the weld testing tool robot controlled may allow the weld to be tested quickly and efficiently. The weld testing tool may be more easily manipulated using the robot.

The method 200 includes generating 212 weld test data based on testing results of the tested spot weld. The weld testing tool may generate ultrasound data that is analyzed to determine if the spot weld is acceptable or if the spot weld is a bad weld.

The method 200 includes providing 214 feedback to the weld analysis tool. The feedback corresponds to the weld test data (e.g., good weld, bad weld, weld nugget diameter, weld nugget shape, and the like). The feedback is used to update the analysis criteria based on the weld test data. The feedback may be used to enforce the analysis criteria. For example, the feedback may verify that the analysis criteria used is correctly identifying bad welds. If a particular spot weld was identified as being bad or suspect, but the spot weld was verified by the weld testing tool as being a good weld, then such feedback is provided to the weld analysis tool, such as to change the analysis criteria. For example, the thresholds may be raised or lowered.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, paragraph (f), unless and until such claim limitations expressly use the phrase "means for" followed by a statement of function void of further structure.

This written description uses examples to disclose the various embodiments, and also to enable a person having ordinary skill in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

The foregoing description of embodiments and examples has been presented for purposes of illustration and description. It is not intended to be exhaustive or limiting to the forms described. Numerous modifications are possible in light of the above teachings. Some of those modifications have been discussed and other will be understood by those skilled in the art. The embodiments were chosen and described for illustration of various embodiments. The scope is, or course, not limited to the examples or embodiments set forth herein, but can be employed in any number of applications and equivalent devices by those of ordinary skill in the art. Rather it is hereby intended the scope be defined by the claims appended hereto. Additionally, the features of various implementing embodiments may be combined to form further embodiments.

What is claimed is:

1. A welding assembly for in-line spot welding using welding electrodes of a welding machine, the welding assembly comprising:
   a non-destructive weld testing system configured to monitor the welding electrodes during spot welding of the spot welds and analyze weld data generated during the spot welding to determine whether a spot weld is an anomaly, the weld testing system comprising:
      a non-destructive weld testing tool mounted on a robot and being robotically controlled, the weld testing tool having a phased-array ultrasonic transducer configured to test spot welds in-line that are determined by the weld testing system to be anomalies; and
      a control module configured to control movement of the weld testing tool to test anomalous spot welds in response to the weld testing system determining that the anomalous spot welds are anomalies.

2. The welding assembly of claim 1, wherein the weld testing system comprises a weld monitoring tool monitoring at least one weld characteristic of the spot welds and generating weld data based on the at least one weld characteristic and a weld analysis tool analyzing the weld data to determine a weld quality of each spot weld based on analysis criteria.

3. The welding assembly of claim 1, wherein the weld testing system monitors at least one of current, voltage, resistance, heat input rate, and total energy input of the welding electrodes for welding each spot weld.

4. The welding assembly of claim 1, wherein the weld testing system analyzes the weld data by comparing the weld data to a threshold weld data and identifies any spot weld having weld data beyond the threshold weld data to be an anomaly that is tested by the weld testing tool.

5. A non-destructive weld testing system for testing spot welds performed by welding electrodes of a welding machine, the weld testing system comprising:
  a weld monitoring tool monitoring at least one weld characteristic of the spot welds, the weld monitoring tool generating weld data based on the at least one weld characteristic;
  a weld analysis tool analyzing the weld data to determine a weld quality of each spot weld based on analysis criteria; and
  a non-destructive weld testing tool configured to test spot welds, wherein the weld testing system causes the weld testing tool to target testing of spot welds in response to the weld analysis tool determining that the spot welds have a weld quality beyond a threshold weld quality, the weld testing tool generating weld test data based on testing results, the weld testing tool providing feedback to the weld analysis tool correlating to the weld test data, the weld analysis tool updating the analysis criteria based on the weld test data.

6. The weld testing system of claim 5, wherein the weld testing tool comprises a phased array ultrasonic transducer.

7. The weld testing system of claim 5, wherein the weld testing tool is mounted on a robot and is robotically controlled to position the weld testing tool for testing the spot welds.

8. The weld testing system of claim 5, wherein the weld testing tool target tests spot welds determined to be anomalies based on the weld quality.

9. The weld testing system of claim 5, wherein the weld analysis tool comprises a database storing the analysis criteria.

10. The weld testing system of claim 5, wherein the weld quality comprises a pass grade or a fail grade for each spot weld based on the analysis criteria, the weld testing tool testing each spot weld receiving a fail grade.

11. The weld testing system of claim 5, wherein the weld characteristics comprise at least one of current, voltage, resistance, heat input rate, and total energy input for welding each spot weld.

12. The weld testing system of claim 5, wherein the analysis criteria comprises thresholds for each weld characteristic corresponding to a threshold weld quality for each weld characteristic, the weld analysis tool analyzing the weld data to determine if the weld data is beyond the corresponding threshold.

13. The weld testing system of claim 12, wherein the thresholds are configured to be changed based on the feedback from the weld testing tool.

14. The weld testing system of claim 5, wherein the weld testing tool measures a nugget diameter of the spot weld.

15. The weld testing system of claim 5, wherein the weld testing tool provides in-line testing of the spot welds.

16. A method of non-destructive weld testing spot welds performed by welding electrodes of a welding machine, the method comprising:
  monitoring at least one weld characteristic of the spot welds;
  generating weld data based on the at least one weld characteristic;
  analyzing the weld data to determine a weld quality of each spot weld based on analysis criteria to determine spot welds that are anomalies;
  testing spot welds in response to the spot welds being determined to be anomalies;
  generating weld test data based on testing results of the tested spot welds; and
  providing feedback correlating to the weld test data to update the analysis criteria based on the weld test data.

17. The method of claim 16, wherein said analyzing the weld data comprises comparing the weld data to a threshold weld data to determine a weld quality.

18. The method of claim 17, wherein said generating weld test data comprises verifying, based on the testing results of the tested spot welds, that the weld data determined to be beyond the threshold weld data corresponds to a spot weld that is an anomaly.

19. The method of claim 16, wherein said monitoring at least one weld characteristic comprises monitoring at least one of current, voltage, resistance, heat input rate, and total energy input for welding each spot weld.

20. The method of claim 16, further comprising storing the weld data in a database.

* * * * *